United States Patent [19]

Onopchenko et al.

[11] 4,018,828
[45] Apr. 19, 1977

[54] PROCESS FOR RECOVERING DIALKYLARYLKETONE

[75] Inventors: Anatoli Onopchenko, Monroeville; Johann G. D. Schulz, Pittsburgh, both of Pa.

[73] Assignee: Gulf Research & Development Company, Pittsburgh, Pa.

[22] Filed: May 27, 1975

[21] Appl. No.: 581,288

[52] U.S. Cl. .................. 260/591; 260/590 FA; 260/590 C; 260/590 R
[51] Int. Cl.$^2$ .......................................... C07C 49/76
[58] Field of Search ................. 260/591, 590 R

[56] References Cited

UNITED STATES PATENTS

| | | | |
|---|---|---|---|
| 3,403,183 | 9/1968 | Dobraty et al. | 260/591 |
| 3,836,845 | 9/1974 | Payne | 260/591 |
| 3,895,071 | 7/1975 | Kablaoui et al. | 260/590 R |

OTHER PUBLICATIONS

Palm, et al., The Chemistry of the Carbonyl Group, pp. 429–458.

Primary Examiner—James O. Thomas, Jr.
Assistant Examiner—James H. Reamer

[57] ABSTRACT

A process for recovering a dialkylarylketone from an oily mixture containing it and largely a 1,1-diaryl-2-nitro-ethylene which comprises adding a base to the mixture until solidification of the dialkylarylketone occurs and then recovering the solid dialkylarylketone.

7 Claims, No Drawings

PROCESS FOR RECOVERING DIALKYLARYLKETONE

BACKGROUND OF THE INVENTION

1. Field of the Invention

The invention defined relates to a process for recovering a dialkylarylketone, normally solid at room temperature, from an oily liquid mixture containing the same.

2. Description of the Prior Art

We are not aware of any pertinent prior art.

SUMMARY OF THE INVENTION

The process defined and claimed herein relates to the recovery of a dialkylarylketone, particularly an alkylbenzophenone, from an oily mixture containing it and largely a 1,1-diaryl-2-nitroethylene which comprises adding a base, particularly sodium hydroxide, to the mixture until solidification of the dialkylarylketone occurs and then recovering the solid dialkylarylketone.

BRIEF DESCRIPTION OF THE PROCESS

The oily mixture containing the dialkylarylketone that is to be recovered herein will contain the following components in the followng amounts:

|  | Parts by Weight | |
|---|---|---|
|  | Broad Range | Narrow Range |
| dialkylarylketone | 25 to 95 | 55 to 90 |
| 1,1-diaryl-2-nitro-ethylene | 5 to 40 | 10 to 30 |

In a preferred embodiment, the oily mixture treated herein is obtained as a result of the nitric acid oxidation of a 1,1-diarylalkane as defined and claimed, for example, in our copending application Ser. No. 581,287, filed concurrently herewith, entitled PROCESS FOR PREPARING DIARYLKETONES. In our said application a 1,1-diarylalkane represented by the following structural formula:

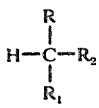

wherein R, and $R_1$, the same or different, are aryl radicals containing one or more rings, at least one of which is an aromatic ring, such as phenyl, biphenyl, naphthyl, phenanthryl, anthryl, indyl, dihydronaphthyl, cyclohexylphenyl, etc., but which is preferably phenyl radical, with the aryl radicals carrying from one to two alkyl substituents thereon, each alkyl substituent having from one to four carbon atoms, and $R_2$ being an alkyl radical having from one to 16 carbon atoms, is subjected to oxidation with critical amounts of nitric acid and water. The organic, or oily product recovered from such operation will contain the following components in the following amounts:

|  | Parts by Weight | |
|---|---|---|
|  | Broad Range | Narrow Range |
| dialkylarylketone | 25 to 95 | 55 to 90 |
| 1,1-diaryl-2-nitro-ethylene | 5 to 40 | 10 to 30 |
| unreacted diarylalkane | 0 to 20 | 1 to 10 |
| unidentified oxidation products | 0 to 15 | 1 to 5 |

In the above, specific examples of dialkylarylketones include:
- 4,4'-dimethylbenzophenone
- 3,3'-dimethylbenzophenone
- 2,2'-dimethylbenzophenone
- 2,3'-dimethylbenzophenone
- 2,4'-dimethylbenzophenone
- 3,4'-dimethylbenzophenone
- 3,4,3',4'-tetramethylbenzophenone
- 3,4,2',3'-tetramethylbenzophenone
- 3,4,2',4'-tetramethylbenzophenone
- 2,3,2',4'-tetramethylbenzophenone
- 2-methyl-4-chloro-3'-ethyl-4'-propylbenzophenone, etc., of 1,1-diaryl-2-nitroethylenes include:
- 1,1-bis(p-tolyl)-2-nitroethylene
- 1,1-bis(p-tolyl)-2-nitropropylene
- 1,1-bis(m-tolyl)-2-nitroethylene
- 1,1-bis(m-tolyl)-2-nitropropylene
- 1,1-bis(o-tolyl)-2-nitroethylene
- 1,1-bis(o-tolyl)-2-nitropropylene
- 1,1-bis(3,4-dimethylphenyl)-2-nitroethylene
- 1,1-bis(3,4-dimethylphenyl)-2-nitropropylene
- 1,1-bis(2,4-dimethylphenyl)-2-nitroethylene
- 1,1-bis(2,4-dimethylphenyl)-2-nitropropylene
- 1-(2-methyl-4-ethylphenyl)-1-(4-chloro-3-cyclohexylphenyl)-2-nitrobutylene, etc., of diarylalkanes include:
- 1,1-bis(p-tolyl)ethane
- 1,1-bis(m-tolyl)-ethane
- 1,1-bis(o-tolyl)ethane
- 1,1-bis(2,3-dimethylphenyl)ethane
- 1,1-bis(3,4-dimethylphenyl)ethane
- 1,1-bis(2,4-dimethylphenyl)ethane
- 1,1-bis(4-ethylphenyl)propane
- 1-(3,4-dimethyl)-1-(3-ethyl-4-iodo)butane, etc.

The unidentified oxidation products are believed to include precursors of diarylketones, such as alcohols, olefins and nitroalcohols of the starting diarylalkane, some ring nitrated products, as well as carboxylic acids of the benzophenone, and some degradation products of the starting material, such as phthalic acids, nitrophthalic acids, toluic acids, trimellitic acid, etc. In some runs, the corresponding dinitroethylene is also formed in cases where the starting 1,1-diarylalkane is 1,1-diarylethane. The specific oily mixtures that are preferably treated herein for recovery of dialkylarylketones therefrom will contain the specific dialkylarylketone, 3,4,3',4'-tetramethylbenzophenone (TMB) or 4,4'-dimethylbenzophenone (DMB); the specific 1,1-diaryl-2-nitroethylene, 1,1-bis(3,4-dimethylphenyl)-2-nitroethylene or 1,1-bis(4-methylphenyl)-2-nitroethylene and the specific unreacted diarylalkane charge, 1,1-bis(3,4-dimethylphenyl)ethane DXE) or 1,1-bis(4-methylphenyl)ethane (DTE).

In accordance with our discovery we add sufficient base to the oily mixture identified above until solidification of the desired dialkylarylketone occurs. In one embodiment, the product is then extracted with a solvent to take up the 1,1-diaryl-2-nitroethylene and any unreacted diarylalkane and/or unidentified oxidation products that may be present to leave behind substantially pure dialkylarylketone as a solid. In a preferred embodiment, the oily product mixture is dissolved in a solvent, and then treated with base until the desired dialkylarylketone solidifies. The remaining components in the product mixture stay in solution and the desired, substantially pure dialkylarylketone can be recovered therefrom in any convenient or conventional manner, for example, by filtration. The processes defined above are preferably carried out at atmospheric temperature and atmospheric pressure, but can also be carried out at an elevated temperature, for example, up to about the boiling point of the solvent employed, or even higher, under an elevated pressure, for example, up to about 500 pounds per square inch gauge (about 35 kilograms per square centimeter).

Any solvent that will maintain the components of the oily mixture in solution can be used above. Examples of solvents suitable herein include alcohols, such as methanol, ethanol, and isopropanol; esters, such as ethyl acetate and methyl formate; ketones, such as acetone and methyl ethyl ketone; acids, such as acetic acid, and propionic acid; ethers, such as tetrahydrofuran and p-dioxane; hydrocarbons, such as benzene, toluene, n-hexane and n-heptane; chlorinated hydrocarbons, such as carbon tetrachloride, chloroform and methylene chloride; "super solvents", such as dimethylsulfoxide, dimethylformamide, and hexamethylphosphoramide; and carbon disulfide. The amount of solvent needed can vary over a wide range but in general will amount to at least about one part by weight per part by weight of the total components in the mixture desired to be maintained in solution, preferably about two to about ten parts by weight.

Suitable bases that can be used herein include sodium hydroxide, potassium hydroxide, calcium hydroxide, ammonia, ammonium hydroxide, sodium amide, potassium amide, potassium t-butoxide, etc. The amount of base used is that amount sufficient to cause the desired dialkylarylketone to solidify when the same is added to the oily mixture being treated. Of these we prefer to employ sodium hydroxide, particularly as an aqueous solution. In general, the amount of base added is the equivalent amount needed to give a basic solution, for example, from about 0.05 to about 20 weight percent of the ketone.

DESCRIPTION OF PREFERRED EMBODIMENTS

EXAMPLE I

A mixture containing 140 grams of 1,1-bis(3,4-dimethylphenyl)ethane (DXE) 330 grams of water and 75 grams of 70 percent aqueous nitric acid was heated under reflux (100° C.) and atmospheric pressure for four hours with vigorous stirring. The reaction mixture was cooled to about 0° C. and the aqueous layer was decanted from the organic layer. The organic layer, amounting to 178 grams, on evaporation to dryness in a rotary evaporator lost about 3.1 grams of water. Analysis of the remainder of the organic layer by gas-liquid chromatography showed the following: 15.2 weight percent DXE, 73.9 weight percent 3,4,3',4'-tetramethylbenzophenone (TMB), 9.6 weight percent 1,1-bis(3,4-dimethylphenyl)-2-nitroethylene and 1.3 weight percent of unidentified material. The above mixture, which was of oily consistency, was divided into twelve portions. To each of eleven portions there was added but a single solvent from the following group sufficient for the resulting solution to contain from about eight to about 10 weight percent of solute: methanol, acetone, n-hexane, benzene, ethyl acetate, carbon tetrachloride, acetic acid, p-dioxane, tetrahydrofuran, trichloromethane and isopropanol. The twelfth portion contained no solvent. Each of the portions was seeded with 0.05 gram of pure TMB, and then maintained at atmospheric pressure and atmospheric temperature for one day. No solid formation was noted. Each of the above solutions was then heated to its boiling point and then allowed to come to room temperature. Again no solids were formed. The solutions were then cooled to −70° C. and then permitted to come to room temperature. This time, too, no solid formation was noted. Each of the solutions was then evaporated on a steam bath to about one-third of its original volume and then cooled to room temperature, but no solids were formed. Accordingly, none of the above procedures was successful in recovering the tetramethylbenzophenone from the oily mixture.

EXAMPLE II

A mixture containing 70 grams of DXE, 330 grams of water and 75 grams of 70 percent aqueous nitric acid was heated while stirring at atmospheric pressure and 100° C. for four hours. The reaction mixture was cooled to about 0° C. and the aqueous layer was decanted from the organic layer. The product was transferred to a rotary evaporator and then evaporated to dryness. Analysis of the oily mixture, which amounted to 83.3 grams, by gas-liquid chromatography showed the following: 9.7 weight percent DXE, 66.0 weight percent TMB, 19.2 weight percent nitroethylene and 5.1 percent of unidentified material. The oily mixture was warmed to 35°–40° C. on a steam bath and a ten percent aqueous solution of sodium hydroxide was slowly added dropwise thereto until solidification of the oily mixture occurred. The amount of aqueous sodium hydroxide used amounted to 10.6 grams. The solids were filtered, washed with 100 grams of cold water twice, and 100 grams of n-hexane at a temperature of 50° C. The recovered solids were dried in a vacuum oven at 120° C. and amounted to 65.2 grams of material, of which 99 weight percent was TMB. The hexane washings were evaporated to dryness in a rotary evaporator, resulting in 23.8 grams of additional product whose composition was as follows: 31.4 weight percent DXE, 15.3 weight percent TMB, 45.6 weight percent nitroethylene and 7.3 weight percent unidentified material. The latter product can be treated in the manner described herein to recover additional TMB therefrom.

EXAMPLE III

A mixture containing 70 grams of DXE, 350 grams of water and 38.0 grams of 70 percent aqueous nitric acid was heated while stirring at atmospheric pressure and 100° C. for 5 hours. The reaction mixture was cooled to about 0° C. and the aqueous layer was decanted from the organic layer. The organic layer was evaporated to dryness in a rotary filter to produce 80 grams of oily product mixture. Analysis by gas chromatography of this material showed the following: 61.3 weight percent TMB, 8.3 weight percent nitroethylene, 27.0 weight percent DXE and 3.4 weight percent of unidentified material. The product was divided into approximately four equal portions, and then dissolved, respectively, in 80 to 100 cubic centimeters of methanol, acetone, ethyl acetate and tetrahydrofuran. To each solution there was added dropwise about 10 cubic centimeters of 10 percent aqueous sodium hydroxide, sufficient for precipitation to occur in each solution. To each of the solutions there was added about five cubic centimeters of concentrated hydrochloric acid, without any apparent effect on the solubility of the solids that had been formed. In each case, however, the color of solution had been significantly improved from brown to off-white or light yellow. Filtration of the solutions, followed by washing of the solids obtained with water and drying in a vacuum oven at 100° C. for 1 hour produced solids analyzing as follows:

TABLE I

| Solvent Used | Grams of Recovered Solids as First Crop | Analysis, Weight Percent TMB |
| --- | --- | --- |
| Methanol | 12.1 | 95.4 |
| Acetone | 10.2 | 94.8 |
| Ethyl Acetate | 11.3 | 95.1 |
| Tetrahydrofuran | 8.0 | 96.0 |

The results obtained above are surprising. It is well known that dialkylarylketones are normally solid at room temperature. For example, the melting point of 3,4,3',4'-tetramethylbenzophenone (TMB) is about 140° C. and that of 4,4'-dimethylbenzophenone (DMB) is about 95° C. It would be expected, therefore, that when the mixture being treated herein is below the melting point of the dialkylarylketone therein little or no difficulty should be experienced in recovery of the dialkylarylketone therefrom, since it would be expected to be solid. However, as shown above, in each case wherein TMB is present, the mixture is oily, and treatment with a large number of solvents did not suffice in separating TMB therefrom. The results herein are further surprising, since no appreciable amount of acid is present in the mixture for reaction with the base, nor is there believed to be any other material therein that would react therewith.

Obviously, many modifications and variations of the invention, as hereinabove set forth, can be made without departing from the spirit and scope thereof, and therefore, only such limitations should be imposed as are indicated in the appended claims.

We claim:
1. A process for recovering a dialkylarylketone selected from the group consisting of 3,4,3',4'-tetramethylbenzophenone and 4,4'-dimethylbenzophenone from an oily mixture containing the same and a 1,1-diaryl-2-nitroethylene, said mixture having been obtained as a result of the nitric acid oxidation of 1,1-bis (3,4-dimethylphenyl)ethane and 1,1-bis(4-methylphenyl)ethane, respectively, which comprises adding a base selected from the group consisting of sodium hydroxide, potassium hydroxide, calcium hydroxide, ammonia, ammonium hydroxide, sodium amide, potassium amide and potassium t-butoxide to said mixture until solidification of said dialkylarylketone occurs, the amount of said base employed ranging from about 0.5 to about 20 weight percent based on said dialkylarylketone, and then recovering said solid dialkylarylketone by separating the latter from a solvent solution of said 1,1-diaryl-2-nitroethylene, the solvent used in said solvent solution selected from the group consisting of hydrocarbons, alcohols, ketones, esters and ethers.
2. The process of claim 1 wherein said base is sodium hydroxide.
3. The process of claim 1 wherein said treated mixture is extracted with said solvent to remove said 1,1-diaryl-2-nitroethylene therefrom.
4. The process of claim 1 wherein said oily mixture is dissolved in said solvent prior to the addition of the base thereto.
5. The process of claim 4 wherein said solvent is selected from the group consisting of methanol, acetone, ethyl acetate and tetrahydrofuran.
6. The process of claim 1 wherein the amount of said solvent is at least about one part by weight per part by weight of the 1,1-diaryl-2-nitroethylene.
7. The process of claim 6 wherein the amount of solvent is about two to about ten parts by weight of the 1,1-diaryl-2-nitroethylene.

* * * * *